United States Patent
Seiver et al.

(10) Patent No.: US 9,550,037 B2
(45) Date of Patent: Jan. 24, 2017

(54) PATIENT CONTROL OF VENTILATION PROPERTIES

(75) Inventors: Adam Seiver, Los Altos Hills, CA (US); Samir Ahmad, San Diego, CA (US); Peter R. Doyle, Vista, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1617 days.

(21) Appl. No.: 12/812,545

(22) PCT Filed: Jan. 9, 2009

(86) PCT No.: PCT/IB2009/050088
§ 371 (c)(1),
(2), (4) Date: Jul. 12, 2010

(87) PCT Pub. No.: WO2009/087607
PCT Pub. Date: Jul. 16, 2009

(65) Prior Publication Data
US 2010/0288279 A1    Nov. 18, 2010

Related U.S. Application Data

(60) Provisional application No. 61/020,428, filed on Jan. 11, 2008.

(51) Int. Cl.
*A61M 16/00* (2006.01)
*G06F 19/00* (2011.01)
(Continued)

(52) U.S. Cl.
CPC ............ *A61M 16/00* (2013.01); *A61M 16/125* (2014.02); *A61M 16/161* (2014.02);
(Continued)

(58) Field of Classification Search
CPC ................... A61M 16/00; A61M 2016/0021; A61M 2016/0036; A61M 2016/102; A61M 16/125; A61M 16/161; A61M 2202/0208; A61M 2202/025; A61M 2205/18; A61M 2205/3355; A61M 2205/3365; A61M 2205/3368; A61M 2205/3553; A61M 2205/3561; A61M 2205/3584; A61M 2205/3592; A61M 2205/505; A61M 2205/52; A61M 2230/04; A61M 2230/10; A61M 2230/202; A61M 2230/205; A61M 2230/50; A61M 2230/63; G06F 19/3481
(Continued)

(56) References Cited

U.S. PATENT DOCUMENTS

| 5,647,346 A | 7/1997 | Holscher |
| 5,927,274 A | 7/1999 | Servidio |

(Continued)

FOREIGN PATENT DOCUMENTS

| EP | 1391215 A1 | 2/2004 |
| EP | 1433456 A1 | 6/2004 |

(Continued)

*Primary Examiner* — Justine Yu
*Assistant Examiner* — Mark K Han (57) ABSTRACT

A ventilator (10) that pressurizes gas from a body of gas to provide a flow of gas to an airway of a subject (14) such that the gas flow mechanically facilitates the respiration of the subject (14). In order to enhance the comfort of the subject (14) during ventilation by the ventilator (10), the ventilator (10) enables the subject (14) to make unsupervised adjustments to one or more of the properties of the gas flow, within predetermined limits.

19 Claims, 3 Drawing Sheets

US 9,550,037 B2

Page 2

(51) Int. Cl.
*A61M 16/12* (2006.01)
*A61M 16/16* (2006.01)
*A61M 16/10* (2006.01)

(52) U.S. Cl.
CPC . *G06F 19/3481* (2013.01); *A61M 2016/0021* (2013.01); *A61M 2016/0036* (2013.01); *A61M 2016/102* (2013.01); *A61M 2202/025* (2013.01); *A61M 2202/0208* (2013.01); *A61M 2205/18* (2013.01); *A61M 2205/3355* (2013.01); *A61M 2205/3365* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2205/52* (2013.01); *A61M 2230/04* (2013.01); *A61M 2230/10* (2013.01); *A61M 2230/202* (2013.01); *A61M 2230/205* (2013.01); *A61M 2230/50* (2013.01); *A61M 2230/63* (2013.01)

(58) Field of Classification Search
USPC ................. 128/203.12, 204.18, 204.21, 204.26, 128/205.24, 205.26, 206.21, 206.28, 206.29, 128/207.12–16, 207.18, 204.23; 137/908
See application file for complete search history.

(56) References Cited

U.S. PATENT DOCUMENTS 6,807,965 B1    10/2004  Hickle
7,225,809 B1 *   6/2007  Bowen et al. ........... 128/204.21

FOREIGN PATENT DOCUMENTS

| JP | H08117340 A | 5/1996 |
| WO | 2006122167 A2 | 11/2006 |
| WO | 2007136411 A2 | 11/2007 |

* cited by examiner

PATIENT CONTROL OF VENTILATION PROPERTIES

PRIORITY CLAIM

This application claims priority to U.S. patent application No. Ser. 61/020,428 filed 11 Jan. 2008, the entire contents of which are incorporated herein by reference.

BACKGROUND OF THE INVENTION

The present invention relates to ventilators, and, more specifically, to a ventilator that enables a patient to control, within predetermined limits, one or more properties of the gas flow provided to the patient by a ventilator.

Ventilators that provide a flow of gas to an airway of a subject are known. Generally, a ventilator generates the gas flow with one or more properties that mechanically facilitate the respiration of the subject. Under some circumstances, ventilation may be uncomfortable for the subject. In order to enhance the comfort of the subject while ventilation is taking place, one or more properties of the flow of gas must be fine-tuned by a caregiver, with feedback from the subject. Typically, subjects are not given control over the properties of the gas flow generated by the ventilator because improper adjustment of the properties of the gas flow presents various risks to the health and/or safety of the subject.

SUMMARY OF THE INVENTION

One aspect of the invention relates to a ventilator that provides a flow of gas for delivery to an airway of a subject. In one embodiment, the ventilator comprises a flow generating system, a processor, and a patient interface. The flow generating system generates the gas flow having one or more properties that facilitate respiration of the subject. The processor controls the flow generating system to control the one or more properties of the gas flow. The patient interface is readily accessible to the subject and receives a selection of an adjustment from the subject for at least one of the one or more properties of the gas flow. The processor is further configured to make the at least one of the one or more properties of the gas flow adjustable via the patient interface within a predetermined range such that (i) if the at least one of the one or more properties of the gas flow will remain within the predetermined range after the selected adjustment received via the patient interface is made, the processor controls the flow generating system to make the selected adjustment, and/or (ii) if the at least one of the one or more properties of the gas flow will fall outside of the predetermined range after the selected adjustment received via the patient interface is made, the processor does not control the flow generating system to make the selected adjustment.

Another aspect of the invention relates to a method of providing a gas flow for delivery to an airway of a subject. In one embodiment, the method comprises generating the gas flow with one or more properties that facilitate respiration of the subject, receiving a selection of an adjustment from the subject for at least one of the one or more properties of the gas flow, making the selected adjustment to the at least one of the one or more properties of the gas flow if the at least one of the one or more properties of the gas flow will remain within a predetermined range after the selected adjustment is made, and declining to make the selected adjustment to the at least one of the one or more properties of the gas flow if the at least one of the one or more properties of the gas flow would not remain within the predetermined range after the selected adjustment.

Another aspect of the invention relates to a system configured to provide a flow of gas for delivery to an airway of a subject. In one embodiment, the system comprises means for generating the gas flow having one or more properties that facilitate respiration of the subject, means for receiving a selection of an adjustment from the subject for at least one of the one or more properties of the gas flow, means for making the selected adjustment to the at least one of the one or more properties of the gas flow if the at least one of the one or more properties of the gas flow will remain within a predetermined range after the selected adjustment is made, and means for declining to make the selected adjustment to the at least one of the one or more properties of the gas flow if the at least one of the one or more properties of the gas flow would not remain within the predetermined range after the selected adjustment.

Another aspect of the invention relates to a ventilator that provides a flow of gas for delivery to an airway of a subject. In one embodiment, the ventilator comprises a flow generating system, a processor, and a patient interface. The flow generating system generates a gas flow having a plurality of properties that facilitate respiration of the subject. The processor controls the flow generating system to control n properties of the gas flow gas. The configuration of the n properties can be represented as a vector in an n-dimensional space, where n is greater than 1. The patient interface is readily accessible to the subject and receives a selection of an adjustment from the subject for at least one of the n properties of the gas flow that are controlled by the processor. The processor is further configured to make the at least one of the n properties of the gas flow adjustable via the patient interface within predetermined boundaries such that (i) if the vector that represents the configuration of the n properties of the gas flow will remain within a predetermined bounded region in the n-dimensional space after the selected adjustment received via the patient interface is made, the processor controls the flow generating system to make the selected adjustment, and/or (ii) if the vector that represents the configuration of the n properties of the gas flow will fall outside of the predetermined bounded region in the n-dimensional space after the selected adjustment is made, the processor does not control the flow generating system to make the selected adjustment. The predetermined bounded region in the n-dimensional space is shaped such that an acceptable range for a given one of the n properties depends on a current level of one or more of the other n properties.

Another aspect of the invention relates to a method of providing a gas flow for delivery to an airway of a subject. In one embodiment, the method comprises generating the gas flow having a plurality of properties that facilitate respiration of the subject and controlling n properties of the gas flow. The configuration of the n properties can be represented as a vector in an n-dimensional space, where n is greater than 1. The process further includes receiving a selection of an adjustment from the subject for at least one of the n properties of the gas flow; making the selected adjustment if the vector that represents the configuration of the n properties of the gas flow will remain within a predetermined bounded region in the n-dimensional space after the selected adjustment is made; and declining to make the selected adjustment if the vector that represents the configuration of the n properties of the gas flow would fall outside of the predetermined bounded region in the n-dimensional space after the selected adjustment. The predetermined bounded region in the n-dimensional space is shaped such that an acceptable range for a given one of the n properties depends on a current level of one or more of the other n properties.

Another aspect of the invention relates to a system configured to provide a flow of gas for delivery to an airway of a subject. In one embodiment, the system comprises means for generating the gas flow having a plurality of properties that facilitate respiration of the subject; means for controlling n properties of the gas flow, wherein the configuration of the n properties can be represented as a vector in an n-dimensional space, and wherein n is greater than 1; means for receiving a selection of an adjustment from the subject for at least one of the n properties of the gas flow; means for making the selected adjustment if the vector that represents the configuration of the n properties of the gas flow will remain within a predetermined bounded region in the n-dimensional space after the selected adjustment is made; and means for declining to make the selected adjustment if the vector that represents the configuration of the n properties of the gas flow of gas would fall outside of the predetermined bounded region in the n-dimensional space after the selected adjustment. The predetermined bounded region in the n-dimensional space is shaped such that an acceptable range for a given one of the n properties depends on a current level of one or more of the other n properties.

Another aspect of the invention relates to a ventilator that provides a flow of gas for delivery to an airway of a subject. In one embodiment, the ventilator comprises a flow generating system, a processor, and a patient interface. The flow generating system generates a gas flow having properties that facilitate respiration of the subject. The processor controls the flow generating system to control the properties of the gas flow. The patient interface is readily accessible to the subject and receives a request an adjustment from the subject for a given one of the properties of the gas flow. The processor is further configured to make the given property of the gas flow adjustable via the patient interface within an acceptable range such that (i) if the given property of the gas flow will remain within the acceptable range after the selected adjustment is made, the processor controls the flow generating system to make the selected adjustment, and/or (ii) if the given property of the gas flow will fall outside of the acceptable range after the selected adjustment is made, the processor does not control the flow generating system to make the selected adjustment. The processor is further configured such that the acceptable range of the given property of the gas flow varies as a function of another one of the properties of the gas flow.

Another aspect of the invention relates to a method of providing a gas for delivery to an airway of a subject. In one embodiment, the method comprises generating the gas flow having properties that facilitate respiration of the subject; receiving a selection of an adjustment from the subject for a given one of the properties of the gas flow; making the selected adjustment to the given property of the gas flow if the given property of the gas flow will remain within an acceptable range after the selected adjustment is made; and declining to make the selected adjustment to the given property of the gas flow if the given property of the gas flow would not remain within the acceptable range after the selected adjustment. The acceptable range of the given property of the gas flow varies as a function of another one of the properties of the gas flow.

Another aspect of the invention relates to a system configured to provide a flow of gas for delivery to an airway of a subject. In one embodiment, the system comprises means for generating the gas flow having properties that facilitate respiration of the subject; means for receiving a selection of an adjustment from the subject for given one of the properties of the gas flow; means for making the selected adjustment to the given property of the gas flow if the given property of the gas flow will remain within an acceptable range after the selected adjustment is made; and means for declining to make the selected adjustment to the given property of the gas flow if the given property of the gas flow would not remain within the acceptable range after the selected adjustment. The acceptable range of the given property of the gas flow varies as a function of another one of the properties of the gas flow.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
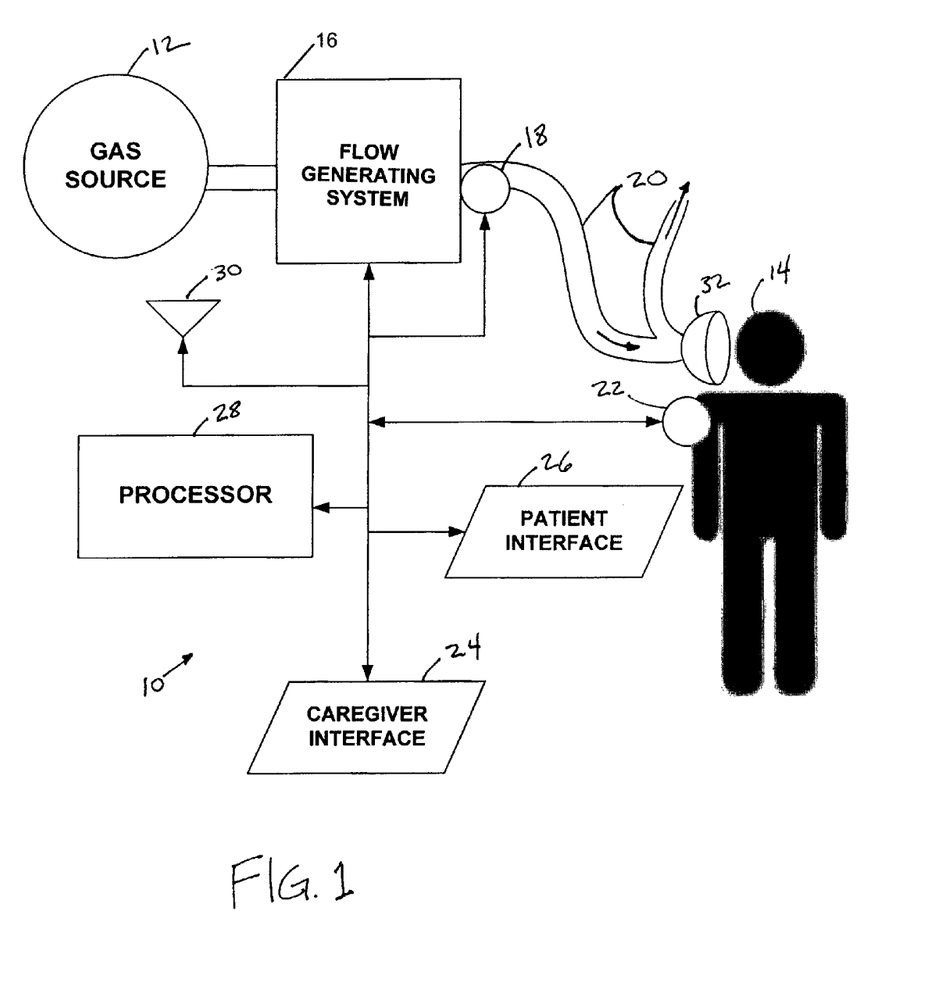
FIG. 1 illustrates a ventilator according to one or more embodiments of the invention.

Turning to FIG. 1, a ventilator 10 is illustrated in accordance with one or more embodiments of the invention. Ventilator 10 pressurizes gas from a body of gas 12 to provide a flow of gas to an airway of a subject 14 such that the gas flow mechanically facilitates the respiration of subject 14. In order to enhance the comfort of subject 14 during ventilation by ventilator 10, ventilator 10 enables subject 14 to make unsupervised adjustments to one or more of the properties of the gas flow, within predetermined limits. In one embodiment, ventilator 10 includes a flow generating system 16, a monitor 18, a patient circuit 20, a patient monitor 22, a caregiver interface 24, a patient interface 26, a processor 28, and/or a transmitter 30.

Body of gas 12 is a supply of gas that is accessible to ventilator 10 for pressurization and delivery to the airway of subject 14. As such, the gas in body of gas 12 is breathable. It should be appreciated that although body of gas 12 is illustrated as a single source of gas, this is not intended to be limiting. In fact, in several embodiments, gas from a plurality of sources (e.g., ambient air, pure oxygen, oxygen enriched gas, helium, etc.) are mixed by ventilator 10 before being delivered to subject 12 in the gas flow. Accordingly, body of gas 12 may include one or more of ambient atmosphere, a wall gas supply, a canister or tank of gas, and/or other sources of breathable gas. In one embodiment, at least a portion of body of gas 12 is already pressurized before it is introduced into ventilator 10. For example, in instances in which body of gas 12 includes gas contained within a pressurized canister, or in a wall gas system, the gas may be pressurized.

Flow generating system 16 is configured to generate the flow of gas that is delivered to the airway of subject 14. In particular, flow generating system 16 includes one or more components (e.g., one or more valves, one or more pressure generators, etc.) that enable flow generating system 16 to control one or more properties of the gas flow such that the gas flow mechanically facilitates the respiration of subject 14. As subject 14 breathes, inhaling and exhaling, the pressure of the gas flow generated by flow generating system 16 rises and falls (rising during inhalation and falling during exhalation). The rise and fall of the pressure of the gas flow forces gas into the lungs of subject 14 during inhalation, and allows gas to escape from (and in some instances even creates suction that pulls gas out of) the airway of subject 14 during exhalation.

If the pressure of the gas flow generated by flow generating system 16 is represented as a plot versus time, the plot would form a periodic waveform as the pressure oscillates with the respiration of subject 14. In one embodiment, one or more properties of the gas flow that are controlled by flow generating system 16 to facilitate the respiration of subject 14 may be conceptualized in terms of the parameters of the waveform formed by the plot of the pressure of the gas flow versus time. For example, the one or more properties controlled by the flow generating system 16 may include the amplitude of the waveform, the frequency of the waveform (i.e., the respiratory rate), the maximum of the waveform (i.e., the peak inhalation pressure), the minimum of the waveform (i.e., the minimum exhalation pressure), the equilibrium value of the waveform, the shape of the waveform (e.g., rise time, etc.), and/or other parameters of the waveform.

Similarly, if the flow rate of the gas flow generated by flow generating system 16 is represented as a plot versus time, the plot of the flow rate would form a periodic waveform as the flow rate oscillates with the respiration of subject 14. One or more properties of the gas flow that are controlled by flow generating system to facilitate the respiration of subject 14 may be conceptualized in terms of the parameters of the waveform of the flow rate versus time. These properties may include properties that are parameters of the plot of pressure versus time (e.g., frequency). Other properties may be unique to the plot of the flow rate versus time, such as, for example, maximum flow rate, minimum flow rate, tidal volume (e.g., the integral of the waveform), the shape of the waveform (e.g., cycling trigger, etc.), and/or other properties.

In some instances, the one or more properties of the gas flow that are controlled by flow generating system 16 include at least one property that is not a parameter of the plot of pressure of the gas flow versus time. For example, the one or more properties may include one or more of a tidal volume, a triggering sensitivity (e.g., an exhalation triggering sensitivity, an inhalation triggering sensitivity, etc.), and/or other properties. A triggering sensitivity is related to the change in pressure detected by ventilator 10 due to the respiration of subject 14 (e.g., due to subject beginning an inhalation, due to subject 14 beginning an exhalation, etc.). A "higher" triggering sensitivity requires a smaller change in pressure to trigger the operation of ventilator 10 to change between modes (e.g., from inhalation to exhalation) than a "lower" triggering sensitivity would.

Monitor 18 includes one or more sensors that detect one or more properties of the gas flow. For example, monitor 18 may include one or more of a flow rate sensor, a pressure sensor, a gas composition sensor, temperature, humidity, and/or other sensors. In some instances, monitor 18 may include sensors that detect various parameters of the operation of one or more components within flow generating system 16 (e.g., valve opening size, motor torque, motor speed, motor current, etc.), as detecting these parameters may enable estimation of the one or more properties of the gas flow being generated by flow generating system 16. Although monitor 18 is illustrated in FIG. 1 as a single component located downstream from flow generating system 16, this is not intended to be limiting. In one embodiment monitor 18 includes a plurality of sensor components. Further, monitor 18 may be partially, or wholly, included within flow generating system 16, as is shown in FIG. 1. The detection of the one or more properties of the gas flow by monitor 18 enables one or more aspects of the control over the gas flow by flow generating system 16 and/or processor 28, as is discussed further below.

The gas flow is carried from flow generating system 16 to subject 14 via patient circuit 20, which can include flexible conduit that carries the gas flow to a patient interface assembly 32. Patient circuit 20 can be a single-limb or dual limb circuit. In the illustrated embodiment, patient circuit 20 is a dual-limb circuit that includes an inspiratory limb and an expiratory limb in the form of a second flexible conduit that conveys gas exhaled from subject 14. in an exemplary embodiment, the expiratory limb is coupled to flow generating system 16. Typically, the expiratory limb is coupled to an expiration valve in the flow generating system to control the release of gas from the expiratory limb. Alternatively, patient circuit 20 may be a single-limb circuit.

Patient interface assembly 32 is either an invasive or non-invasive patient interface appliance or assembly for communicating the gas flow to the airway of subject 14. For example, patient interface assembly 32 may include a nasal mask, nasal/oral (full) mask, total face mask (that covers the face), nasal cannula, endotracheal tube, or tracheal tube. Patient interface assembly 32 may also include a headgear assembly or other assembly, such as mounting straps or a harness, for removing and fastening the patient interface appliance to the patient.

Patient monitor 22 includes one or more devices that detect one or more physiological functions of subject 14. For example, patient monitor 22 may include one or more of an inhaled gas, an exhaled gas, or a blood gas sensor (e.g., oxygen saturation sensor, carbon dioxide saturation sensor, etc.), a cardio-vascular sensor (e.g., a pulse sensor, a pulse shape sensor, an electrocardiogram, a cardiac output sensor, etc.), a temperature sensor, an actimeter, an electroencephalogram (e.g., processer and/or raw), and/or other sensors. As is discussed further below, information generated by patient monitor 22 may be implemented in a feedback manner to control one or more aspects of the operation of ventilator 10. It should be appreciated that although patient monitor 22 is illustrated in FIG. 1 as a single entity, patient monitor 22 may include a plurality of sensors disposed at disparate locations on and/or about subject 14. The present invention further contemplates that the one or more patient monitors 22 communicate with processor 28 via a hard-wired or wireless communication link.

Caregiver interface 24 is configured to provide an interface between ventilator 10 and a caregiver of subject 14 (e.g., a doctor, a technician, a respiratory therapist, a nurse, an orderly, a researcher, etc.) through which the caregiver may provide information to and receive information from ventilator 10. This enables data, results, alarms, or machine generated diagnostics, assessments, or recommendations and/or instructions and any other communicable items, collectively referred to as "information," to be communicated between the caregiver and ventilator 10. For instance, the caregiver may configure one or more settings of ventilator 10 that dictate the manner in which one or more of the properties gas flow generated by flow generating system 16 are controlled. As such, the caregiver interface 24 may be generally inaccessible (at least for practical purposes) to subject 12 because improper adjustment of these settings may have undesirable results. In one embodiment, the inaccessibility of caregiver interface 24 to subject 14 is a result of an electronic security (e.g., password protection, etc.) and/or the location of caregiver interface 24 with respect to subject 14.

Examples of interface devices suitable for inclusion in caregiver interface 24 include a keypad, buttons, switches, a keyboard, knobs, levers, a display screen, a touch screen, speakers, a microphone, an indicator light, an audible alarm, and a printer. It should be understood that other communication techniques, either hard-wired or wireless, are also contemplated by the present invention for inclusion in caregiver interface 24. For example, the present invention contemplates that caregiver interface 24 may be integrated with a removable storage interface. In this example, information may be loaded into ventilator 10 from removable storage (e.g., a smart card, a flash drive, a removable disk, etc.) that enables the caregiver(s) to customize the implementation of ventilator 10. Other exemplary input devices and techniques adapted for use with ventilator 10 as caregiver interface 24 include, but are not limited to, an RS-232 port, RF link, an IR link, and/or modem (telephone, cable, ethernet or other). In short, any technique (hard-wired or wireless) for communicating information with ventilator 10 is contemplated by the present invention as caregiver interface 24.

Patient interface 26 is configured to provide an interface between ventilator 10 and subject 14 through which subject 14 may provide information to and receive information from ventilator 10. As such, patient interface 26 may include any of the interface devices discussed above with respect to caregiver interface 24. In particular, in one embodiment, patient interface 26 is configured to accept inputs to ventilator 10 from subject 14 that correspond to selected adjustments to one or more of the properties of the gas flow generated by flow generating system 16.

As mentioned above, providing subject 14 with substantially unfettered control over the properties of the gas flow may be undesirable. Accordingly, as is discussed further below, ventilator 10 is configured such that the control over the properties of the gas flow provided to subject 14 via patient interface 26 is restricted to adjustments to the properties that fall within predetermined limits. Thus, while subject 14 may be able to adjust the gas flow (via patient interface 26) to make ventilation more comfortable, the predetermined limits maintain the safety of the ventilation.

In one embodiment, patient interface 26 includes a completely separate device, or set of devices, from caregiver interface 24. In this embodiment, patient interface 26 may be located in a convenient location for access by subject 14. For example, patient interface 26 may be located at or near the bedside of subject 14, attachable to or provided on the bedding of subject 14, attachable to or provided on a chair or sofa on which subject 14 is sitting (or lying), provided integrally with or attachable to patient circuit 20 (e.g., at or near delivery assembly 32). The present invention further contemplates that patient interface 26 communicates with processor 28 via a hard-wired or wireless communication link.

Processor 28 is configured to provide information processing capabilities in ventilator 10. As such, processor 28 may include one or more of a digital processor, an analog processor, a digital circuit designed to process information, an analog circuit designed to process information, a state machine, and/or other mechanisms for electronically processing information. Although processor 28 is shown in FIG. 1 as a single entity, this is for illustrative purposes only. In some implementations, processor 28 may include a plurality of processing units. These processing units may be physically located within the same device, or processor 28 may represent processing functionality of a plurality of devices operating in coordination. For example, in one embodiment, the functionality attributed below to processor 28 is divided between a first processor contained within a housing that is common to the first processor and one or more components of flow generating system 16, and a second processor that communicates with the first processor at least periodically to obtain information generated by the first processor and further process the obtained information. In this embodiment, the second processor of processor 28 may include a processor provided by an external computer terminal.

Processor 28 is configured to control flow generating system 16 as the flow generating system generates and/or controls the gas flow that is delivered to the airway of subject 14. As such, processor 28 can control flow generating system 16 to selectively adjust the properties of the gas flow. As can be seen in FIG. 1, processor 28 is in operative communication with each of flow generating system 16, monitor 18, caregiver interface 24, and patient interface 26. This communication may be achieved via any suitable communication link (e.g., dedicated channel/line, via a network, wired, wireless, etc.).

The communication between monitor 18 and processor 28 enables processor 28 to determine current levels of one or more of the properties of the gas flow that is being delivered to the airway of the patient. For example, as mentioned above, monitor 18 may detect one or more of a flow rate, a volume, a pressure, a composition, a temperature, humidity, and/or other properties or combination of properties of the gas flow and may communicate information related to these properties to processor 28. Processor 28 then implements the information received from monitor 18 in a feedback manner to control the properties of the gas flow.

From caregiver interface 24, a caregiver can configure one or more of the properties controlled by flow generating system 16. In fact, in one embodiment, the functionality of processor 28 and caregiver interface 24 includes the functionality provided by a processor and interface in a conventional ventilator to enable a caregiver to configure the properties of the gas flow that will be delivered to a patient during ventilation. As such, processor 28 may further provide information to the caregiver via caregiver interface 24 that enables the caregiver to monitor the properties of the generated gas flow as it is delivered to subject 14.

Processor 28 is further configured to make at least one of the one or more properties of the gas flow that are controlled by the flow generating system 16 adjustable by subject 14. As mentioned above, via patient interface 26, subject 14 can input selections for adjustments to one or more of the properties of the gas flow into processor 28. Processor 28 then effects the adjustments, provided that the adjustments do not cause the properties of the gas flow to breach predetermined limits. This enables subject 14 to customize the properties of the gas flow (within predetermined limits) to enhance the comfort of the ventilation. The one or more properties of the gas flow that subject 14 is able to adjust via patient interface 26 may include one or more of a respiratory rate, a tidal volume, an inhalation pressure, an exhalation pressure, a triggering sensitivity, and/or other properties.

In one embodiment, processor 28 is configured to enable subject 14 to adjust a given property of the gas flow, via patient interface 26, within a predetermined range. Accordingly, in response to the reception of a selection of an adjustment to the given property from subject 14 via patient interface 26, processor 28 determines if making the selected adjustment will take the given property outside of a predetermined acceptable range for the given property. If processor 28 determines that making the selected adjustment will not cause the given property to leave the predetermined range, then processor 28 controls flow generating system 26 to modify the given property of the gas flow in accordance with the selected adjustment. On the other hand, if processor determines that making the selected adjustment will cause the given property to leave the predetermined range, then processor 28 declines to make the selected adjustment.

In one embodiment, in addition to declining to make the selected adjustment if the selection would cause the given property to leave the predetermined range, processor 28 makes a modified adjustment that adjusts the given property to the edge of the predetermined range. This will enhance the comfort of subject 14 in response to the selected adjustment without adjusting the given property outside of the predetermined range.

In one embodiment, in response to a selection of an adjustment that would cause the given property to leave the predetermined range, processor 28 provides an alert to subject 14 that the selected adjustment would cause the given property to leave the predetermined range. For example, processor 28 may provide the alert to subject 14 via patient interface 26. The present invention also contemplates providing this alert to a caregiver, for example, via caregiver interface 24. Processor 28 can provide these alerts to subject 14, the caregiver, or both in instances where no adjustment is made to the given property, or in instances where a modified adjustment is made to the given property. Further, in one embodiment, alerts are provided to subject 14 and/or the caregiver even if the given property is within the predetermined range to inform subject 14 of whether a subsequent adjustment would cause the given property to leave the predetermined range.

In one embodiment, the predetermined limits that limit the customization of adjustable properties of the gas flow are not determined and implemented individually for each of the adjustable properties. Instead, a set of properties within the adjustable properties that are related to each other may be grouped such that the predetermined limits of a given one of the set of properties depends on the current levels of the other properties in the set. For example, the tidal volume (i.e., the volume of air taken in during a single inhalation and exhaled during a single exhalation) may be related to the respiratory rate (e.g., as the tidal volume increases, the respiratory rate required for satisfactory oxygenation may drop). As such, these two properties of the gas flow may be grouped such that the acceptable range for one of these properties depends on a current level of the other. For example, if the respiratory rate is decreased in response to a selection received from subject 14 via patient interface 26, then the acceptable range for the tidal volume is increased.

Figure 2:
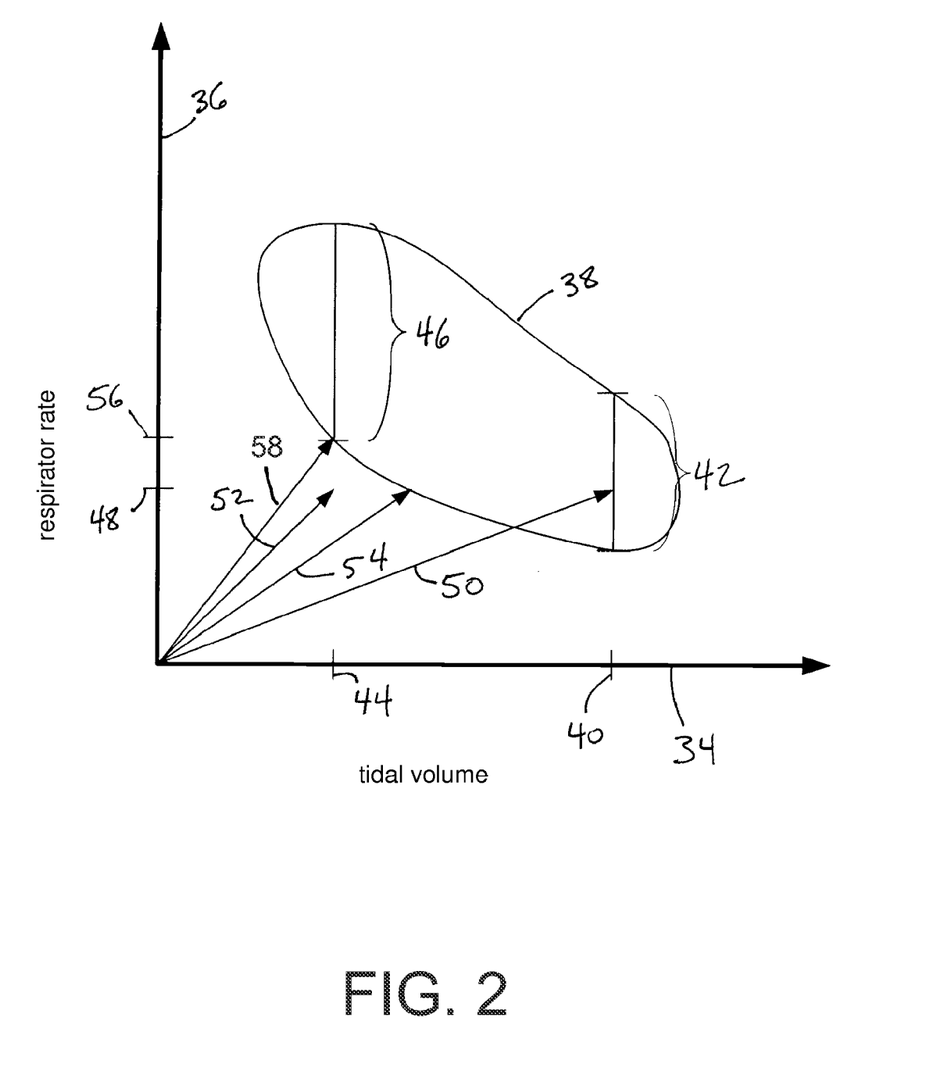
FIG. 2 illustrates a vector space according to one or more embodiments of the invention.

The grouping and interdependence of a set of properties of the gas flow can be conceptualized using a vector space. For example, FIG. 2 illustrates a two dimensional vector space that graphically depicts the interdependence between tidal volume and respiratory rate described above. The space can be described in terms of a first axis 34 that corresponds to tidal volume and a second axis 36 that corresponds to respiratory rate. The predetermined limits for these properties can be described in the space as a predetermined region 38 that encompasses all of the acceptable combinations of tidal volume and respiratory rate. As can be appreciated from FIG. 2, predetermined region 38 is shaped such that an acceptable range for one of the properties depends on the current level of the other property (if predetermined region 38 was bounded entirely by boundaries parallel to axis 34 and 36, there would be no interdependence between the adjustable properties). More specifically, if the tidal volume is at a first tidal volume level 40, predetermined region 38 defines a first acceptable range 42 for respiratory rate. If the tidal volume is adjusted to a second tidal volume level 44 (e.g., in accordance with a selection from subject 14 via patient interface 26), then predetermined region 38 defines a second acceptable range 46 for respiratory rate.

In the space represented in FIG. 2, a single configuration of the tidal volume and the respiratory rate can be represented as a vector, with the levels (or values associated with the levels) of each of these properties as a coordinate. For example, if the tidal volume is at first tidal volume level 40 and the respiratory rate is at a first respiratory rate level 48, then the configuration of these properties can be represented by a configuration vector 50 that falls within predetermined region 38.

If an adjustment is selected for one of the properties in a grouped set of adjustable properties by subject 14 via patient interface 26, processor only makes the selected adjustment if the adjustment does not cause the configuration vector representing the configuration of the set of properties after the adjustment is made to fall outside of the predetermined region for the set of properties. By way of illustration, if the tidal volume and respiratory rate of the gas flow are initially at the configuration represented by configuration vector 50, an adjustment may be selected by subject 14 via patient interface 26 to change the tidal volume from first tidal volume level 40 to second tidal volume level 44. If this adjustment were made by processor 28, the new configuration of tidal volume and respiratory rate would be represented by a new configuration vector 52. As can be seen in FIG. 2, configuration vector 52 falls outside of predetermined region 38. Therefore, processor 28 would not make the selected adjustment.

Where a selected adjustment to a given property would cause the configuration vector representing a set of adjustable properties of the gas flow to fall outside of their corresponding predetermined region, processor 28, in addition to declining to make the selected adjustment, may make a modified adjustment to one or more of the set of adjustable properties. The modified adjustment adjusts the given property specified in the selected adjustment, but does not cause the configuration vector representing the group of properties to fall outside of the predetermined region. Instead the modified adjustment adjusts the set of properties such that the configuration vector falls at or near the boundary of the predetermined region. This will enhance the comfort of subject 14, without the exposing subject 14 to the risks associated with adjusting the set of properties of the gas flow such that the configuration vector representing the set of properties falls outside of the predetermined region.

Referring to FIG. 2, in one embodiment, processor 28 receives a selection from subject 14 via patient interface 26 to make an adjustment to the tidal volume that would cause the configuration of tidal volume and respiratory rate to change from configuration vector 50 to configuration vector 52. Because configuration vector 52 is outside of predetermined range 38, processor 28 declines to make the adjustment, but instead makes a modified adjustment. The modified adjustment includes adjusting the tidal volume in the manner selected by subject 14 (e.g., decreasing the tidal volume), but instead of adjusting it all the way to the configuration represented by vector 52, processor 28 causes the tidal volume to be adjusted so that the configuration of the tidal volume and respiratory rate is represented by a configuration vector 54 that falls at or near the boundary of predetermined region 38.

In another embodiment, the same selection is made by subject 14 (i.e., from configuration vector 50 to configuration vector 52). In response to this selection, processor 28 makes the full selected adjustment to tidal volume (i.e., to second tidal volume level 44) and modifies the adjustment by further modifying one or more of the other properties in the set (in this case, adjusts the respiratory rate to a second respiratory rate level 56) such that a configuration vector 58 representing the configuration of the properties falls at or near the boundary of the predetermined region.

In one embodiment, processor 28 provides an alert to subject 14 in response to a selection of an adjustment that would cause the configuration vector of the set of adjustable properties to fall outside of the predetermined region. This alert may be provided to subject 14 via patient interface 26. The alert may be provided in instances in which no adjustment is made in response to the selection or in instances in which a modified adjustment is made based on the selection. In certain implementations where a modified adjustment is made and an alert is provided to subject 14, the alert informs subject 14 of the modifications made to the adjustment in order to keep the configuration vector of the resulting configuration of the adjustable properties of the gas flow within the predetermined region.

It should be appreciated that although FIG. 2 depicts a two-dimensional space for a set of two adjustable properties of the gas flow generated by ventilator 10, this is not intended to be limiting. Any set of n (where n is an integer greater than 1) related properties of the gas flow could be controlled in coordination in the manner described above and illustrated in FIG. 2. For example, the configuration of the n properties can be represented as a configuration vector in an n-dimensional space where the levels (or values associated with the levels) is a coordinate in the configuration vector, and the set of allowable configurations for the set of adjustable properties can be described by a predetermined, n-dimensional region in the vector space.

In one embodiment, n equals 3, with the 3 adjustable properties being pressure support (e.g., the pressure maintained at the airway of subject 14 during respiration), a cycling trigger (e.g., the % of peak flow during inhalation at which the pressure provided by ventilator 10 is reduced to allow exhalation), and a rise time (e.g., the time that it takes for the pressure and/or flow rate of the gas flow to go from its minimum value to its maximum value. Each of these properties, if adjusted by subject 14, may impact the amount of ventilation provided to subject 14 by ventilator 10. In order to provide a degree of customization to subject 14, a region of a 3 dimensional space (where each dimension corresponds to one of the three properties enumerated above) is determined.

Via patient interface 26, subject 14 may adjust one or more of the adjustable properties within the predetermined region. In one embodiment, the predetermined region may be determined to correspond to a range of amounts of ventilation that are to be provided to the patient. For example, the predetermined region may be determined to keep the minute ventilation, the alveolar ventilation, and/or other measurements of ventilation within a predetermined range. In some instances, the amount of ventilation may be monitored, in addition to the three adjustable properties, to ensure that the amount of ventilation remains within the predetermined range. If it is determined that the amount of ventilation has left the predetermined range, the predetermined region defined in the 3-dimensional space that corresponds to pressure support, cycling threshold, and rise time may be reconfigured to bring the amount of ventilation back into its predetermined range.

Referring back to FIG. 1, as was mentioned above, from caregiver interface 24, a caregiver can configure one or more of the properties controlled by flow generating system 16. In one embodiment, this includes configuring the predetermined limits within which the one or more properties of the gas flow will be adjusted in response to a selection from subject 14 via patient interface 26. For example, where a single property of the gas flow is adjustable via patient interface 26 independent from any other adjustable properties, caregiver interface 24 enables the caregiver to configure the predetermined range within which the property of the gas flow can be adjusted by processor 28 in response to a selection for an adjustment from patient interface 26. In some instances, this may include setting one or both of the boundaries of the range manually, setting a width of the range manually, setting a midpoint of the range manually, and/or configuring other aspects of the predetermined range manually. In some instance, one or more aspects of the predetermined range are configured manually via caregiver interface 24, and other aspects are configured by predefined defaults (which may themselves be configured via caregiver interface 24) managed by processor 28. For example, a caregiver may manually specify a midpoint of the predetermined range via caregiver interface 24, and processor 28 then implements the specified midpoint with a default width of the range as the predetermined range.

As was set forth above, in one embodiment, a set of adjustable properties of the gas flow generated by ventilator 10 are controlled in a coordinated manner such that the acceptable range for one of the properties in the set of adjustable properties is a function of the current levels of one or more of the other properties in the set of adjustable properties. In this embodiment, the coordinated control of the set of adjustable properties can be conceptualized as being confined to a predetermined region within a vector space, as was discussed above with respect to FIG. 2. In some instances, one or more aspects of this predetermined region are configured from caregiver interface 24. These aspects may include one or more of a shape of the predetermined region, a dimension of the predetermined region, a function describing the predetermined region, and/or other aspects of the predetermined region. Configuration of the aspects of the predetermined region may include one or both of manually configuring one or more of the aspects of the predetermined region specifically for subject 14 and/or having one or more aspects of the predetermined region defined according to one or more predefined defaults. In some instances, the one or more predefined defaults are also configurable via caregiver interface 24. In other embodiments, the ranges and/or limits (and/or properties thereof) are pre-programmed, with no ability to be altered.

In one embodiment, processor 28 implements information from patient monitor 22 in the control of the one or more properties of the gas flow generated by flow generating system 16. In some instances, the predetermined limits within which subject 14 is enabled to adjust the properties of the gas flow are restricted and/or expanded based on information received from patient monitor 22. By way of non-limiting example, if the information received from patient monitor 22 indicates a change in blood gas of subject 14 (e.g., a rise or drop in oxygen or carbon dioxide), the predetermined limits may be expanded, contracted, and/or shifted to account for the change. In one embodiment, the manner in which processor 28 adjusts the predetermined limits based on information received from patient monitor 22 is configurable for the caregiver via caregiver interface 26. For instance, the caregiver may set one or more thresholds for one or more physiological functions, at which the predetermined limits are to be adjusted. In some instances, the caregiver may configure a proportionality constant (or some other parameter of a function) that defines the relationship between one or more physiological functions of subject 14 and the predetermined limits.

Transmitter 30 transmits information to and receives information from one or more computing entities (e.g., processors, memory, etc.) that are located remotely from ventilator 10. This enables a caregiver to monitor the treatment of subject 14 and/or the operation of ventilator 10 remotely from subject 14 (e.g., at a control center that monitors a plurality of subjects and/or ventilators). In one embodiment, the information transmitted from processor 28 to a remotely located computing entity includes information related to the properties of the gas flow being generated/controlled by ventilator 10. This enables a caregiver with access to the external computing entity to monitor the treatment of subject 14 remotely from the bedside of subject 14.

In one embodiment, the information transmitted from processor 28 to a remotely located computing entity includes information related to the selection of adjustments to the gas flow that are being input by subject 14 to patient interface 26. This information enables the remotely located caregiver to monitor the comfort of subject 14. For example, if subject 14 repeatedly selects adjustments to the gas flow that are not made by ventilator 10 (e.g., because they would cause the properties of the gas flow to leave the predetermined limits), the caregiver may assume that subject 14 is uncomfortable, and may re-assess the current configuration of the properties of the gas flow to determine if an alternate configuration exists that would enhance the comfort of subject 14 without putting her at risk.

In one embodiment, the information transmitted from processor 28 to a remotely located computing entity includes information related to one or more of the physiological functions of subject 14 that are monitored by patient monitor 22. This information enables the remotely located caregiver to monitor the physiological impact of the ventilation on subject 14. Based on this information, the caregiver may assess the effectiveness of various aspects of the ventilation including the current levels of the properties of the gas flow and/or the predetermined limits within which subject 14 is able to adjust the properties of the gas flow.

Figure 3:
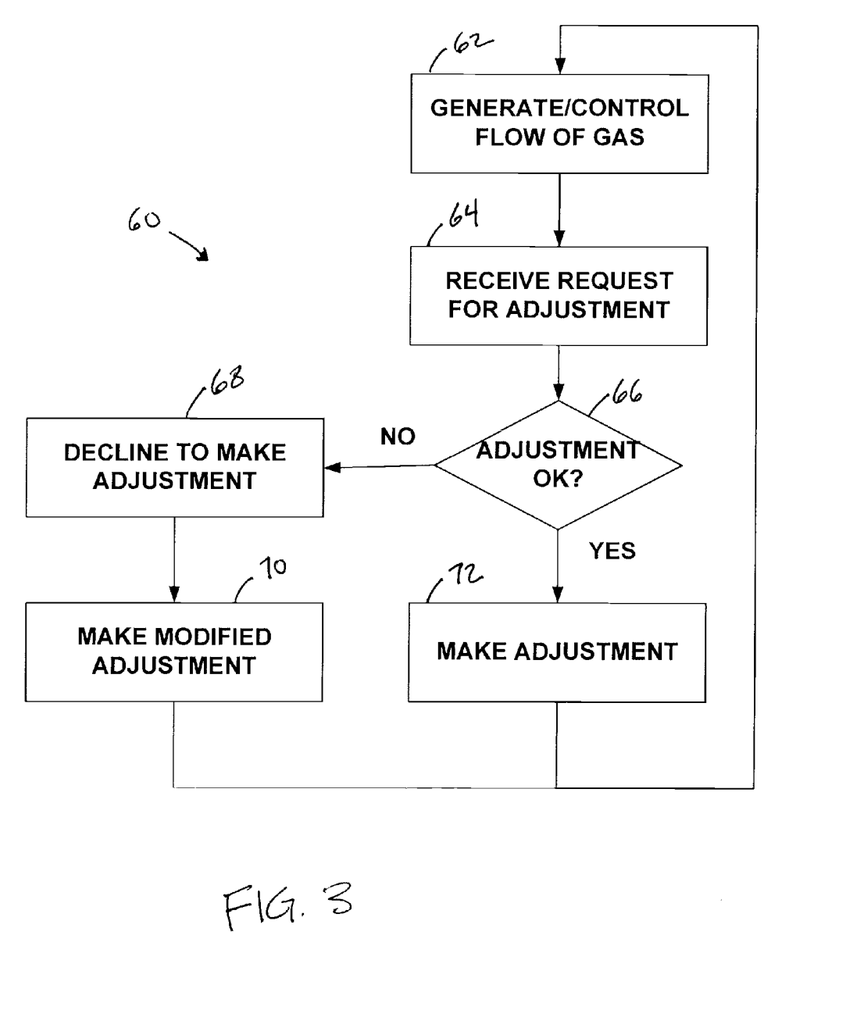
FIG. 3 illustrates a method of providing a flow of gas for delivery to an airway of a subject, in accordance with one or more embodiments of the invention.

FIG. 3 illustrates a method 60 of providing a gas flow for delivery to an airway of a subject, wherein the gas flow has one or more properties that facilitate the respiration of the subject. Although the operations of method 60 are discussed below with respect to the components of ventilator 10 described above and illustrated in FIG. 1, it should be appreciated that this is for illustrative purposes only, and that method 60 may be implemented with alternative components and/or systems without departing from the scope of this disclosure.

At an operation 62, the gas flow is generated such that the one or more properties are controlled to facilitate the respiration of the subject. As has been discussed above, the one or more properties may include one or more of a tidal volume, a triggering sensitivity, a parameter of a waveform formed by a plot of the pressure of the gas flow versus time, and/or other properties. In one embodiment, operation 62 is performed by a flow generating system similar to or the same as flow generating system 16 (shown in FIG. 1 and described above) under the control of a processor similar to or the same as processor 28 (shown in FIG. 1 and described above).

At an operation 64, a selection for an adjustment to a given property of the gas flow is received from the subject. In one embodiment, the selection is received by a processor similar to or the same as processor 28 (shown in FIG. 1 and described above) from a patient interface similar to or the same as patient interface 26 (shown in FIG. 1 and described above).

At an operation 66, a determination is made as to whether the properties of the gas flow will remain within predetermined limits if the adjustment selected at operation 64 is made. In one embodiment, the predetermined limits include a predetermined range for the given property. In one embodiment, the predetermined limits include an acceptable range for the given property that varies as a function of one or more of the other properties of the gas flow. In one embodiment, the given property is one of a set of n properties that are adjusted in a coordinated manner. In this embodiment, the configuration of the set of n properties can be represented as a configuration vector in an n-dimensional vector space, and the predetermined limits are a predetermined region within the n-dimensional vector space. In one embodiment, operation 66 is performed by a processor the same as or similar to processor 28 (shown in FIG. 1 and described above).

If a determination is made at operation 66 that the properties of the gas flow will not remain within the predetermined limits after the selected adjustment is made, then method 60 proceeds to an operation 68, where implementation of the adjustment is declined. In one embodiment, operation 68 is performed by a processor the same as or similar to processor 28 (shown in FIG. 1 and described above).

In one embodiment, method 60 proceeds from operation 68 back to operation 62. In one embodiment, method 60 proceeds from operation 68 to an operation 70, at which a modified adjustment is made to the given property. The modified adjustment includes an adjustment to the given property, but maintains the properties of the gas flow within the predetermined limits. In one embodiment, operation 70 is performed by a flow generating system the same as or similar to flow generating system 16 (shown in FIG. 1 and described above) under the control of a processor the same as or similar to processor 28 (shown in FIG. 1 and described above).

If a determination is made at operation 66 that the properties of the gas flow will remain within the predetermined limits after the selected adjustment is made, then method 60 proceeds to an operation 72, where the adjustment to the given property is made. In one embodiment, operation 72 is performed by a flow generating system the same as or similar to flow generating system 16 under the control of a processor similar to or the same as processor 28 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A ventilator that provides a flow of gas for delivery to an airway of a subject, the ventilator comprising:
    a flow generating system adapted to generate a gas flow having a plurality of properties that facilitate respiration of a subject;
    a processor adapted to control the flow generating system to control one or more of the plurality of properties of the gas flow; and
    a patient interface that is readily accessible to the subject and is adapted to receive a selection of an adjustment from the subject for at least a selected one of the properties of the gas flow,
    wherein the processor is configured to make at least the selected one of the properties of the gas flow (a) adjustable via the patient interface, and (b) restricted to adjustments to current levels of the selected one of the properties that fall within a predetermined acceptable range for the selected one of the properties to maintain a safety of ventilation for the subject, such that: (i) when the selected one of the properties of the gas flow will remain within the predetermined acceptable range to maintain the safety of the ventilation after the selected adjustment received via the patient interface is made, the processor controls the flow generating system to make the selected adjustment, and (ii) when the selected one of the properties of the gas flow will fall outside of the predetermined acceptable range to maintain the safety of the ventilation after the selected adjustment received via the patient interface is made, the processor does not control the flow generating system to make the selected adjustment which prevents an improper adjustment that could expose the subject to risks to health and/or safety,
    wherein the processor is configured to determine the predetermined acceptable range for the selected one of the properties of the gas flow based on a current value of a second one of the properties of the gas flow, wherein the processor changes the predetermined acceptable range for the selected one of the properties of the gas flow in response to a change in the current value of the second one of the properties of the gas flow.

2. The ventilator of claim 1, wherein the processor is configured such that if the selected one of the properties of the gas flow will fall outside of the predetermined acceptable range after the selected adjustment is made, the processor controls the flow generating system to adjust the selected one of the properties of the gas flow to an edge of the predetermined acceptable range.

3. The ventilator of claim 1, further comprising a transmitter that transmits information related to the plurality of properties of the gas flow and information related to selected adjustments to a computing entity that is located remotely from the ventilator.

4. The ventilator of claim 1, wherein the selected one of the properties of the gas flow that is adjustable via the patient interface comprises one of a respiratory rate, a tidal volume, an inhalation pressure, a triggering sensitivity, or an exhalation pressure.

5. The ventilator of claim 1, wherein a plot of the pressure of the gas flow versus time is a waveform, and wherein the selected one of the properties of the gas flow that is adjustable via the patient interface comprises a parameter of the waveform.

6. The ventilator of claim 1, wherein a plot of the flow rate of the gas flow versus time is a waveform, and wherein the selected one of the properties of the gas flow that is adjustable via the patient interface comprises a parameter of the waveform.

7. The ventilator of claim 1, wherein the processor is configured such that if the selected one of the properties of the gas flow will fall outside of the predetermined range after the selected adjustment is made, the processor provides an alert to the subject.

8. The ventilator of claim 1, wherein the selected one of the properties is a respiratory rate and the second one of the properties is tidal volume, and wherein the predetermined acceptable range for the respiratory rate changes when the current value of the tidal volume changes.

9. The ventilator of claim 1, wherein the selected one of the properties is a first one of a respiratory rate, a tidal volume, an inhalation pressure, a triggering sensitivity, and an exhalation pressure, and the second one of the properties is a second one of the respiratory rate, the tidal volume, the inhalation pressure, the triggering sensitivity, and the exhalation pressure.

10. The ventilator of claim 1, wherein the processor is configured to determine the predetermined acceptable range for the selected one of the properties of the gas flow further based on a current value of a third one of the properties of the gas flow, wherein the processor also changes the predetermined acceptable range for the selected one of the properties of the gas flow in response to a change in the current value of the third one of the properties of the gas flow.

11. The ventilator of claim 1, further comprising at least one patient monitor configured to monitor at least one physiological function of the subject, wherein the processor is configured to adjust the predetermined acceptable range for the selected one of the properties of the gas flow further based on data received from the at least one patient monitor.

12. A ventilator that provides a flow of gas for delivery to an airway of a subject, the ventilator comprising:
    a flow generating system adapted to generate a gas flow having one or more properties that facilitate respiration of a subject;
    a processor adapted to control the flow generating system to control the one or more properties of the gas flow;
    a patient interface that is readily accessible to the subject and is adapted to receive a selection of an adjustment from the subject for at least one of the one or more properties of the gas flow, and
    a caregiver interface that is separate from the patient interface,
    wherein the processor is configured to make the at least one of the one or more properties of the gas flow (a) adjustable via the patient interface and (b) restricted to adjustments to current levels of the at least one of the one or more properties that fall within a predetermined acceptable range to maintain a safety of ventilation for the subject, such that (l) if the at least one of the one or more properties of the gas flow will remain within the predetermined acceptable range to maintain the safety of the ventilation after the selected adjustment received via the patient interface is made, the processor controls the flow generating system to make the selected adjustment, and/or (ii) if the at least one of the one or more properties of the gas flow will fall outside of the predetermined acceptable range to maintain the safety of the ventilation after the selected adjustment received via the patient interface is made, the processor does not control the flow generating system to make the selected adjustment which prevents an improper adjustment that could expose the subject to risks to health and/or safety, and wherein the predetermined acceptable range is configurable by the caregiver via the caregiver interface.

13. The ventilator of claim 12, wherein the processor is configured such that when the selected one of the properties of the gas flow will fall outside of the predetermined range after the selected adjustment is made, then the processor provides an alert to the subject.

14. A ventilator that provides a flow of gas for delivery to an airway of a subject, the ventilator comprising:

a flow generating system configured to generate a gas flow having a plurality of properties that facilitate respiration of a subject, the plurality of properties including a set of at least two properties;

a processor adapted to control the flow generating system to control the plurality of properties of the gas flow; and a patient interface that is readily accessible to the subject and is adapted to receive a selection of an adjustment from the subject for a selected one property of the set of properties of the gas flow, wherein the processor is configured to make the selected one property of the set of properties of the gas flow: (a) adjustable via the patient interface, and (b) restricted to adjustments to current levels of the selected one property the set of properties such that the set of properties falls within a predetermined acceptable range to maintain a safety of ventilation for the subject, such that (i) when the set of properties of the gas flow will remain within the predetermined acceptable range to maintain the safety of the ventilation after the selected adjustment received via the patient interface is made, the processor controls the flow generating system to make the selected adjustment, and (ii) when the set of properties of the gas flow will fall outside of the predetermined acceptable range to maintain the safety of the ventilation after the selected adjustment received via the patient interface is made, the processor does not control the flow generating system to make the selected adjustment which prevents an improper adjustment that could expose the subject to risks to health and/or safety.

15. The ventilator system of claim 14, wherein the processor is configured such that if the selected one property of the set of properties of the gas flow will fall outside of the predetermined acceptable range after the selected adjustment is made, the processor controls the flow generating system to adjust the selected one property of the set of properties of the gas flow to cause the set of properties to be at an edge of the predetermined acceptable range.

16. The ventilator system of claim 14, wherein the predetermined acceptable range is configurable by the caregiver via the caregiver interface.

17. The ventilator of claim 14, wherein the set of properties of the gas flow comprises at least two of a respiratory rate, a tidal volume, an inhalation pressure, a triggering sensitivity, or an exhalation pressure.

18. The ventilator of claim 14, wherein the set of properties of the gas flow comprises at least three properties.

19. The ventilator of claim 14, wherein the processor is configured such that when the set of the properties of the gas flow will fall outside of the predetermined range after the selected adjustment is made, then the processor provides an alert to the subject.

* * * * *